United States Patent
Uematsu et al.

(10) Patent No.: US 9,442,127 B2
(45) Date of Patent: Sep. 13, 2016

(54) SAMPLE PROCESSING DEVICE, SAMPLE PROCESSING METHOD, AND REACTION CONTAINER USED IN THESE DEVICE AND METHOD

(75) Inventors: Chihiro Uematsu, Kawasaki (JP); Muneo Maeshima, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 945 days.

(21) Appl. No.: 13/516,157

(22) PCT Filed: Dec. 8, 2010

(86) PCT No.: PCT/JP2010/072006
§ 371 (c)(1),
(2), (4) Date: Jun. 14, 2012

(87) PCT Pub. No.: WO2011/074456
PCT Pub. Date: Jun. 23, 2011

(65) Prior Publication Data
US 2012/0309104 A1     Dec. 6, 2012

(30) Foreign Application Priority Data
Dec. 16, 2009   (JP) ................. 2009-285343

(51) Int. Cl.
*G01N 35/10*       (2006.01)
*B01L 3/02*        (2006.01)
*G01N 35/00*       (2006.01)

(52) U.S. Cl.
CPC ............ *G01N 35/10* (2013.01); *B01L 3/0275* (2013.01); *G01N 35/0098* (2013.01); *B01L 2200/0647* (2013.01); *B01L 2200/143* (2013.01);

(Continued)

(58) Field of Classification Search
CPC .................................................. G01N 35/0098
USPC ........................................................ 436/174
See application file for complete search history.

(56) References Cited

U.S. PATENT DOCUMENTS 5,138,868 A * 8/1992 Long ............................ 73/1.79
5,389,339 A * 2/1995 Petschek et al. ............... 422/64
(Continued)

FOREIGN PATENT DOCUMENTS

CN       1862260 A     11/2006
CN     101255417 A      9/2008
(Continued)

OTHER PUBLICATIONS

Chinese Office Action dated Nov. 20, 2013 (seven (7) pages).
(Continued)

*Primary Examiner* — Christopher A Hixson
*Assistant Examiner* — Emily Berkeley
(74) *Attorney, Agent, or Firm* — Crowell & Moring LLP

(57) ABSTRACT

This invention concerns a sample processing device capable of efficiently recovering biological molecules, such as nucleic acids or proteins. The sample processing device is capable of placing a reaction container having a plurality of reaction sites, and it comprises a nozzle mechanism with a nozzle capable of attaching and removing a dispenser tip for dispensing a solution into the reaction sites of the reaction container and a magnetic tip for generating a magnetic field that allows magnetic beads to migrate to a space among the plurality of reaction sites in the reaction container, and a drive control unit controlling the nozzle mechanism.

6 Claims, 26 Drawing Sheets

(52) U.S. Cl.
CPC ... *B01L2300/0829* (2013.01); *B01L 2400/043* (2013.01); *G01N 2035/1048* (2013.01); *Y10T 436/25* (2015.01)

(56) References Cited

U.S. PATENT DOCUMENTS

| | | | |
|---|---|---|---|
| 5,647,994 | A | 7/1997 | Tuunanen et al. |
| 5,699,794 | A * | 12/1997 | Fleck .......................... 600/310 |
| 6,409,925 | B1 | 6/2002 | Gombinsky et al. |
| 6,468,810 | B1 * | 10/2002 | Korpela ........................ 436/526 |
| 6,764,859 | B1 | 7/2004 | Kreuwel et al. |
| 2006/0120926 | A1 | 6/2006 | Takada et al. |
| 2006/0144169 | A1 | 7/2006 | Porat et al. |
| 2006/0254933 | A1 | 11/2006 | Adachi et al. |
| 2007/0180935 | A1 * | 8/2007 | Angus .................. B01L 3/0279 73/864.14 |
| 2008/0171337 | A1 | 7/2008 | Miyazaki et al. |
| 2008/0248586 | A1 * | 10/2008 | Tajima .................... B01L 3/502 436/164 |
| 2010/0291666 | A1 * | 11/2010 | Collier et al. ............. 435/287.2 |

FOREIGN PATENT DOCUMENTS

| | | |
|---|---|---|
| JP | 8-511721 A | 12/1996 |
| JP | 10-90280 A | 4/1998 |
| JP | 2002-504685 A | 2/2002 |
| JP | 2003-504195 A | 2/2003 |
| JP | 2004-203390 A | 7/2004 |
| JP | 2008-167722 A | 7/2008 |
| JP | 2008-525037 A | 7/2008 |

OTHER PUBLICATIONS

Chinese Office Action dated Apr. 11, 2014 (nine pages).
Japanese Office Action dated May 7, 2014 with English translation (12 pages).
International Search Report with English translation dated Mar. 1, 2011 (eight (8) sheets).
Form PCT/ISA/237 (five (5) sheets).
Boom et al., "Rapid and Simple Method for Purification of Nucleic Acids", Journal of Clinical Microbiology, 1990, vol. 28, No. 3, pp. 495-503 (ten (10) sheets).

* cited by examiner

SAMPLE PROCESSING DEVICE, SAMPLE PROCESSING METHOD, AND REACTION CONTAINER USED IN THESE DEVICE AND METHOD

TECHNICAL FIELD

The present invention relates to a sample processing device and a sample processing method for implementing various types of processing associated with extraction, separation, purification, and other forms of processing of biological molecules, such as nucleic acids and proteins, originally in a sample containing cells, bacteria, viruses, and the like. Also, the present invention relates to a reaction container used in such sample processing device and sample processing method.

BACKGROUND ART

Separation or purification of biological molecules, such as nucleic acids, from biological samples, such as blood, blood plasma, or tissue slice samples, is a fundamental, important procedure in order to obtain test substances in industries involved with diagnosis, plant variety improvement for agricultural crops, food inspection, and the like, as well as for research on life phenomena in biological, biochemical, medical, or other fields. Regarding nucleic acid testing, in particular, polymerase chain reaction (PCR) techniques capable of DNA or RNA amplification have become common. Thus, demands for the separation and the purification of purified nucleic acids that can be amplified via PCR are increasing. In addition to PCR techniques, various nucleic acid amplification techniques, such as the nucleic acid sequence-based amplification (NASBA) technique, the strand displacement amplification (SDA) technique, the self-sustained sequence replication (3SR) technique, the transcription-mediated amplification (TMA) technique, the Qβ replicase amplification technique, and the loop-mediated isothermal amplification (LAMP) technique, have been developed. Accordingly, the nucleic acid testing application range is expanding, and it is considered that demands for separation and purification of nucleic acids from biological samples will keep increasing.

Phenol/chloroform extraction has been known as a technique for separating and purifying a nucleic acid such as DNA or RNA from a biological sample. This technique, however, imposed serious burdens on those performing it due to the use of organic solvent or complicated procedures. In order to overcome the drawbacks described above, a method utilizing the ability of nucleic acids to bind to silica or glass fibers in the presence of a chaotropic agent (e.g., Non-Patent Document 1) was proposed, and an automatic apparatus for implementing nucleic acid extraction was developed (e.g., Patent Document 1).

The process of nucleic acid separation and purification that is generally carried out with the use of an automatic apparatus is as described in (1) to (6) below: (1) cells are fractured with a solution containing a chaotropic agent or surfactant to elute nucleic acids in the solution; (2) silica-coated magnetic beads (i.e., magnetic silica particles) are added to the solution and mixed therein to allow nucleic acids to adsorb onto the particle surface; (3) a magnet is brought into approximate contact therewith from the outside of a reaction container, and a solution containing unnecessary substances, such as proteins, is removed with the use of a pump or other means while magnetic beads remain captured in the reaction container; (4) a wash solution is added to the reaction container, and unnecessary substances are allowed to migrate into the solution; (5) a magnet is brought into approximate contact therewith from the outside of a reaction container again, and a solution containing unnecessary substances is removed while magnetic beads remain captured in the reaction container; and (6) magnetic beads are introduced into sterilized water or low-salt buffer after the wash solution has been removed in order to elute nucleic acids from the magnetic bead surfaces.

PRIOR ART DOCUMENTS

Patent Document

Patent Document 1: JP Patent Publication (Kohyo) No. 2003-504195 A

Non-Patent Document

Non-Patent Document 1: Boom, R.; Sol, C. J. A.; Salimans, M. M. M.; Jansen, C. L.; Wertheimvan Dillien, P. M. E.; and van der Noordaa, J., J. Clin. Microbiol., 28, 495-503, 1990

SUMMARY OF THE INVENTION

Object to be Attained by the Invention

As described above, various types of processing can be carried out with the use of an automatic apparatus when performing separation, extraction, purification, and other forms of processing of biological molecules, such as nucleic acids, from biological samples. Practical application of an automatic apparatus that implements various types of processing remained problematic due to insufficient recovery efficiency after separation, extraction, and purification of biological molecules, the complicated structure of the apparatuses used, and the difficulty of effective recovery of biological molecules.

Accordingly, the present invention is intended to provide a sample processing device and a sample processing method that allows effective recovery of biological molecules such as nucleic acids and proteins and that are suitable for practical applications, as well as a reaction container used in such device and method.

Means for Attaining the Object

The sample processing device according to the present invention, which has attained the above object, is capable of placing a reaction container having a plurality of reaction sites, and it comprises a nozzle mechanism with a nozzle capable of attaching and removing a dispenser tip for dispensing a solution into the reaction sites of the reaction container and a magnetic tip for generating a magnetic field that allows magnetic beads to migrate to a space among the plurality of reaction sites in the reaction container, and a drive control unit controlling the nozzle mechanism.

It is preferable that the nozzle comprise an apical end to attach the dispenser tip and the magnetic tip mounted thereon and a middle region having a larger diameter than that of the apical end, wherein the middle region is capable of attaching a magnetic tip cover.

In addition, the sample processing device according to the present invention may comprise a tip rack that accommodates the sample dispenser tip, a magnetic tip rack that accommodates the magnetic tip, and a cover rack that accommodates the magnetic tip cover.

The drive control unit is capable of controlling the nozzle mechanism to migrate to the reaction container, the tip rack, the magnetic tip rack, and the cover rack, and it is also capable of controlling the nozzle mechanism to migrate so as to mount the dispenser tip, the magnetic tip, and the magnetic tip cover on the nozzle.

The sample processing device may further comprise a reagent rack that can accommodate a reagent bottle filled with a reagent used for recovering biological molecules from biological samples. Examples of the biological molecules include nucleic acids, and the sample processing device according to the present invention is capable of recovering nucleic acids.

Further, it is preferable that, in case that a plurality of reaction containers are placed, the nozzle mechanism comprise a plurality of nozzles corresponding to given reaction sites in each of the plurality of reaction containers.

In addition, the sample processing device according to the present invention preferably comprises a cover-removing mechanism that removes the magnetic tip cover from the nozzle and retains the magnetic tip cover while the apical end of the magnetic tip cover has been inserted into the reaction site.

The cover-removing mechanism may comprise an upper retainer plate and a lower retainer plate opposed to each other with an interval therebetween, so as to sandwich a fringe region of the magnetic tip cover and a notch region provided on one side surface of the upper retainer plate and the lower retainer plate.

The sample processing method according to the present invention, which has attained the above object, comprises a step of soaking magnetic beads having the capacity for nucleic acid adsorption in a solution containing nucleic acids at a given reaction site and a subsequent step of allowing the magnetic beads that had adsorbed nucleic acids to migrate from the given reaction site through oil to another reaction site.

The sample processing method according to the present invention may further comprise a step of soaking the magnetic beads that had adsorbed nucleic acids in a wash solution in the other reaction site and a subsequent step of allowing the magnetic beads to migrate through oil to another reaction site.

In addition, the sample processing method according to the present invention may further comprise a step of soaking the magnetic beads that had adsorbed nucleic acids in an eluent in the other reaction site so as to elute nucleic acids in the eluent.

In the sample processing method of the present invention, it is particularly preferable that a nozzle mounting a magnetic tip generating a magnetic field and a magnetic tip cover surrounding the outer periphery of the magnetic tip be used to capture the magnetic beads and allow them to migrate.

Magnetic beads can be removed from the magnetic tip cover by removing the magnetic tip cover from the nozzle while the magnetic tip cover remains inserted into the reaction site. In such a case, the nozzle may be lifted while sandwiching a fringe region of the magnetic tip cover between an upper retainer plate and a lower retainer plate opposed to each other with a given interval therebetween, so that the magnetic tip cover can be removed from the nozzle.

The sample processing method according to the present invention can involve the use of a reaction container provided with a plurality of reaction sites and an empty space that can be filled with oil above the reaction sites.

In the sample processing method according to the present invention, the given reaction site may be filled with a solution containing biological samples and a chaotropic agent.

The reaction container according to the present invention, which had attained the above object, comprises a plurality of reaction sites and a cover-removing mechanism that removes the magnetic tip cover from the nozzle and retains the magnetic tip cover while the magnetic tip cover mounted on the nozzle has been inserted into the reaction site.

The cover-removing mechanism may comprise an upper retainer plate and a lower retainer plate opposed to each other with an interval therebetween, so as to sandwich a fringe region of the magnetic tip cover and a notch region provided on one side surface of the upper retainer plate and the lower retainer plate.

It is particularly preferable that the notch region be provided at a position such that it is exposed to the openings of the plurality of reaction sites.

In addition, the reaction container according to the present invention preferably comprises an empty space that can be filled with the oil above the openings of the reaction sites.

This description includes part or all of the contents as disclosed in the description and/or drawings of Japanese Patent Application No. 2009-285343, which is a priority document of the present application.

Effects of the Invention

With the use of the sample processing device, the sample processing method, and the reaction container used in such device and method according to the present invention, biological molecules, such as nucleic acids and proteins, can be effectively recovered. Accordingly, application of the present invention realizes practical use of a sample processing device that is excellent in terms of biological molecule recovery efficiency.

EMBODIMENTS FOR CARRYING OUT THE INVENTION

Hereafter, the sample processing device, the sample processing method, and the reaction container used for such device and method according to the present invention are described in detail with reference to the figures.

Figure 1:
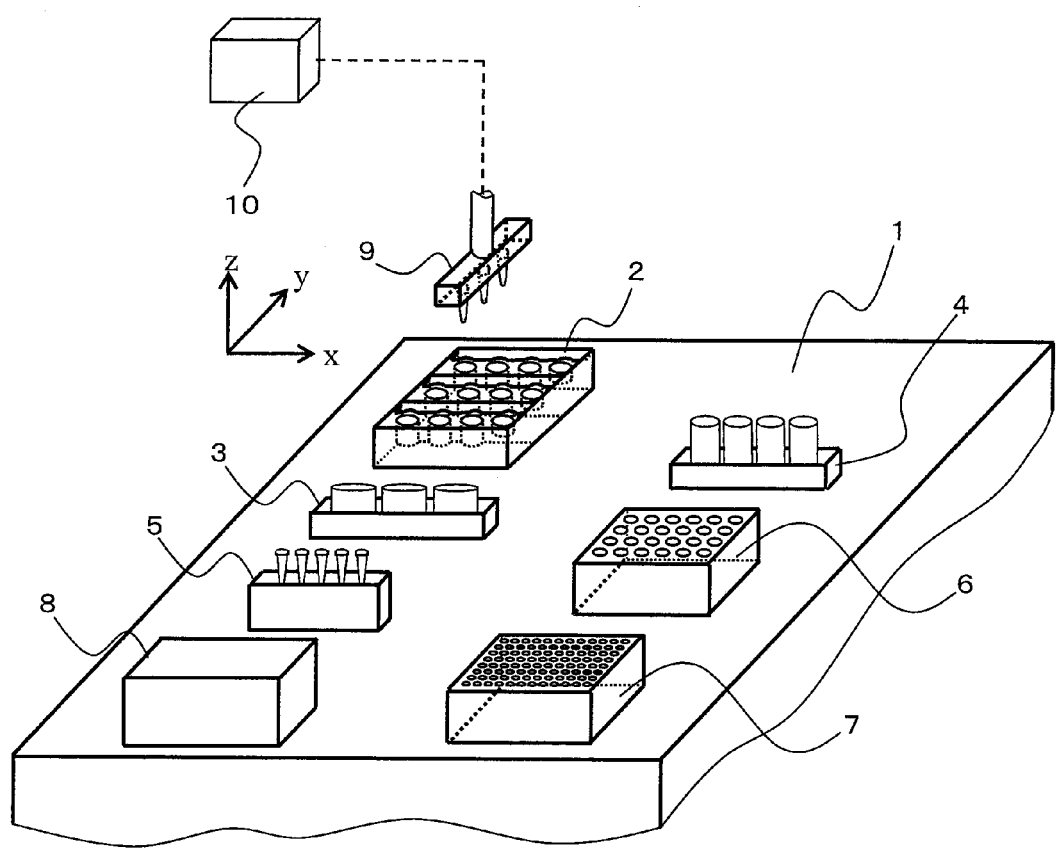
FIG. 1 is a perspective view schematically showing an embodiment of the sample processing device according to the present invention.

As shown in FIG. 1, the sample processing device performs various types of processing of biological samples with the use of the reaction containers 2, in which a plurality of reaction containers 2 are placed in given positions on one surface of a stage 1. The sample processing device comprises a stage 1, a reagent rack 3 capable of accommodating a plurality of reagent bottles, an analyte rack 4 capable of accommodating a sample container filled with target biological samples, a magnetic tip rack 5 accommodating a plurality of magnetic tips, a cover rack 6 accommodating a plurality of magnetic tip covers, a tip rack 7 accommodating a plurality of disposable tips, a waste container 8 used for discarding a waste, a nozzle mechanism 9 arranged movably at a position facing a surface of the stage 1, and a drive control unit 10 controlling the migration and the positioning of the nozzle mechanism 9. The sample processing device also comprises a computer for inputting processing conditions, information on biological samples, and various other types of information (not shown).

The term "biological samples" used herein refers to: biological samples obtained from animals, including humans, such as blood, blood plasma, tissue slices, body fluids, and urine samples; cells, such as animal, plant, and insect cells; microorganisms, such as bacteria, fungi, and algae; and viruses, including virus-infected cells, although the biological samples are not particularly limited thereto. The term "biological samples" also refers to culture solutions in which such cells, microorganisms, and viruses have been cultured and suspensions of such cells, microorganisms, or viruses. The biological samples include biological molecules that are the targets of separation, extraction, or purification implemented by the sample processing device. The term "biological molecules" used herein refers to nucleic acids such as DNA or RNA, proteins such as enzymes or antibodies, and peptide fragments. The targets of separation, extraction, or purification implemented by the sample processing device are not limited to nucleic acids, proteins, and peptide fragments, and compounds produced from cells or microorganisms, including organic compounds or low-molecular-weight compounds, can be subjected to separation, extraction, and purification as biological molecules.

Figure 2:
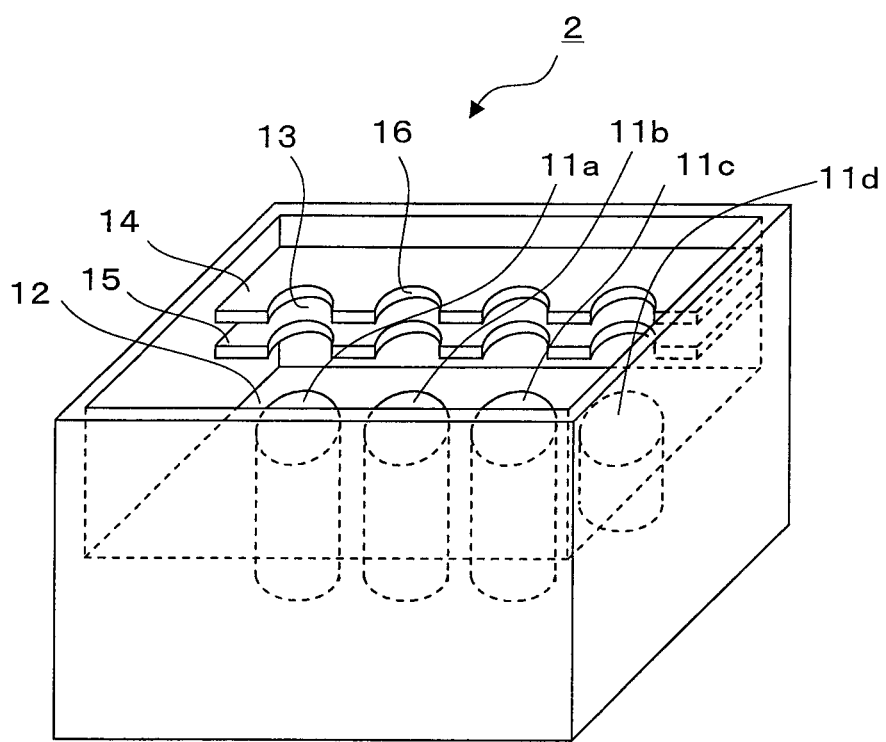
FIG. 2 is a perspective view showing a reaction container used in the sample processing device.
Figure 3:
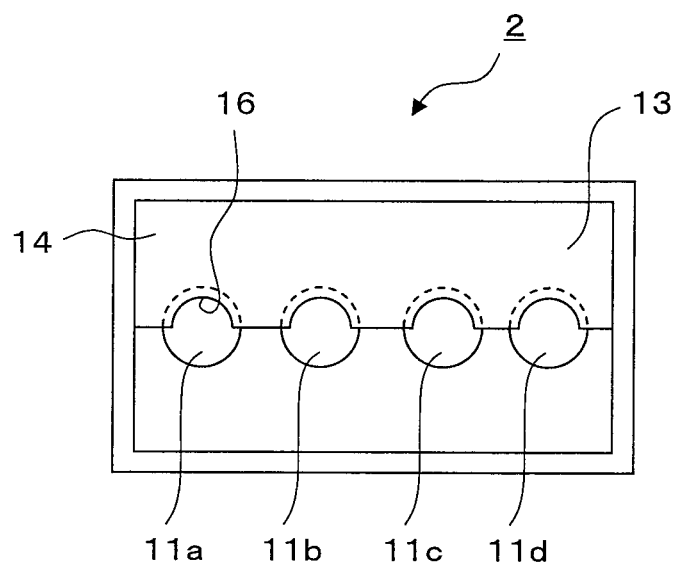
FIG. 3 is a top view showing the reaction container.
Figure 4:
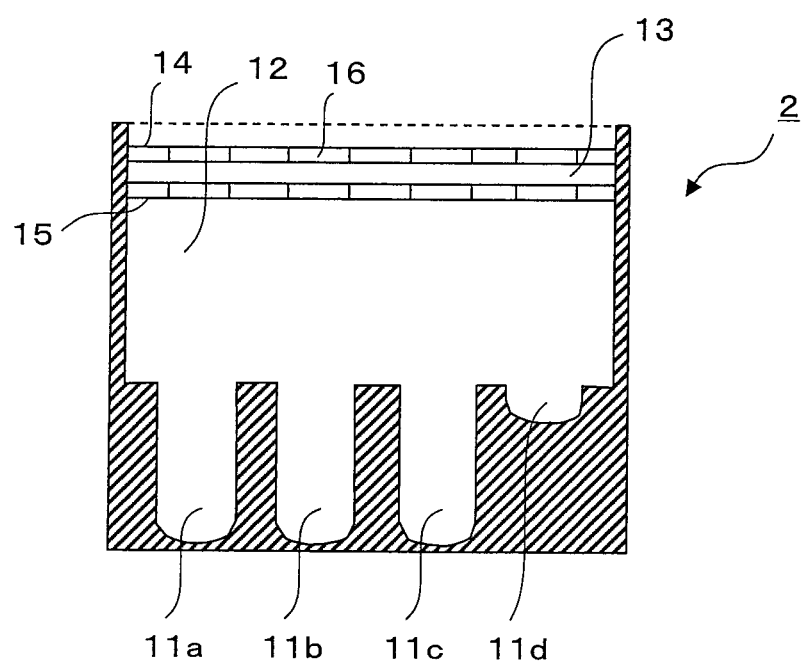
FIG. 4 is a cross-sectional view showing the reaction container.

In the sample processing device, the reaction container 2 has an approximately box-shaped form as a whole, as shown in FIGS. 2 to 4. The reaction container 2 comprises a plurality of reaction sites 11a to 11d for dispensing various reagents. The plurality of reaction sites 11a to 11d are provided in concave form in order to realize given volumes. In this embodiment, the depth of the concavity constituting the reaction site 11d is shallower than that of the reaction sites 11a to 11c, so as to make the volume of the reaction site 11d smaller than that of the reaction sites 11a to 11c. In the reaction container 2, the number of reaction sites and the volume of each reaction site are not particularly limited, and such number and volume can be adequately determined in accordance with the types of processing performed on biological samples. Alternatively, the sample processing device can comprise a reaction container 2 composed of a different number of reaction sites each with a different volume in accordance with the types of processing performed on biological samples.

The reaction container 2 comprises an empty space 12 surrounded by side walls above the opening ends of the plurality of reaction sites 11a to 11d. That is to say, the reaction container 2 comprises an empty space 12 constituted by four side walls and a surface exposed to the opening ends of the plurality of reaction sites 11a to 11d. Further, the reaction container 2 comprises a cover-removing mechanism 13 for removing a magnetic tip cover mounted on the nozzle mechanism 9.

The cover-removing mechanism 13 comprises an upper retainer plate 14 and a lower retainer plate 15 for retaining the magnetic tip cover. The upper retainer plate 14 and the lower retainer plate 15 are arranged approximately parallel to each other with a given interval. The upper retainer plate 14 and the lower retainer plate 15 each comprise a notch region 16 facing each of the plurality of reaction sites 11a to 11d and fitting the external dimensions of the magnetic tip cover. The notch region 16 is provided in such a manner that the end surface thereof is positioned to the inside of the openings of the reaction sites 11a to 11d, when the reaction container 2 is observed from the above.

Figure 5:
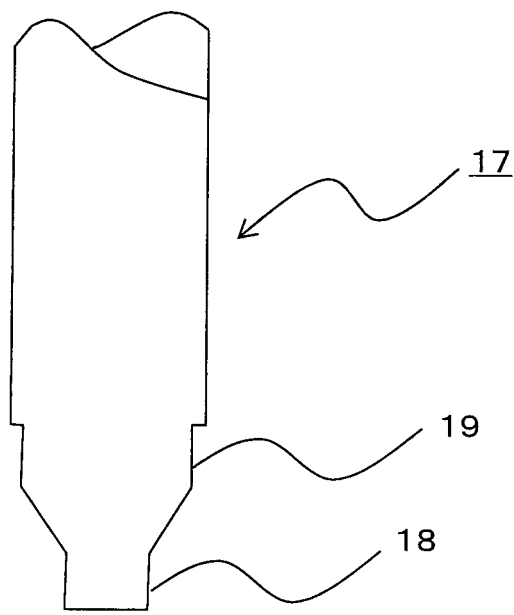
FIG. 5 is a plain view showing a nozzle of the sample processing device.

The nozzle mechanism 9 of the sample processing device comprises a plurality of nozzles 17 as shown in FIG. 5. The nozzle mechanism 9 comprises at least a greater number of nozzles 17 than the reaction containers 2. In other words, the number of the reaction containers 2 that can be provided in the sample processing device is smaller than the number of the nozzles 17. More specifically, about 8 to 12 nozzles 17 can be aligned, for example. By aligning the nozzles 17, the processing capacity per unit time (i.e., a throughput) can be improved.

The inside of a nozzle 17 is in a tubular form and it is connected to a suction/discharge drive apparatus, such as a pump means (not shown). A nozzle 17 comprises an apical end 18 with the smallest diameter and a middle region 19 with a larger diameter than that of the apical end 18.

Figure 6:
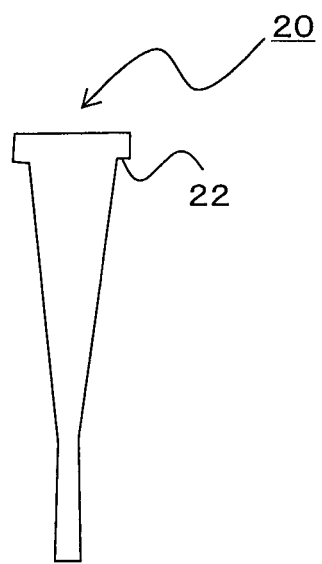
FIG. 6 is a plain view showing a disposable tip removable from the nozzle.
Figure 7:
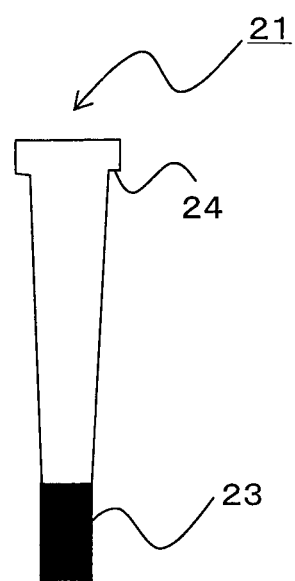
FIG. 7 is a plain view showing a magnetic tip removable from the nozzle.

The disposable tip 20 shown in FIG. 6 and the magnetic tip 21 shown in FIG. 7 can be selectively mounted on the apical end 18 of the nozzle 17. The inner diameter of the base end of each of the disposable tip 20 and the magnetic tip 21 is substantially the same as that of the apical end 18 of the nozzle 17, and it is tapered toward the apical end. Thus, the disposable tip 20 and the magnetic tip 21 can be fitted into the nozzle 17 by inserting the apical end 18 of the nozzle 17 into the base end. The disposable tip 20 comprises a fringe region 22 at the base end. A magnetic tip 21 comprises a magnetic substance 23 that generates a magnetic field at its end and a fringe region 24 at the base end. The magnetic tip 21 can be prepared by inserting the magnetic substance 23 into the apical end of a dispenser tip such as the disposable tip 20.

Figure 8:
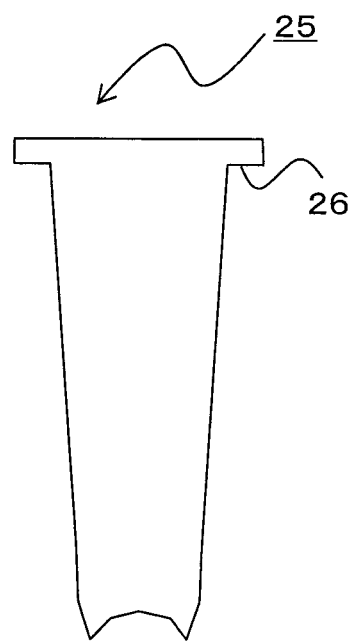
FIG. 8 is a plain view showing a magnetic tip cover removable from the nozzle.

A magnetic tip cover 25 shown in FIG. 8 can be mounted on the middle region 19 of the nozzle 17. The inner diameter of the base end of the magnetic tip cover 25 is substantially the same as that of the middle region 19 of the nozzle 17, and it is also tapered toward the apical end. Thus, the magnetic tip cover 25 can be fitted into the nozzle 17 by inserting the middle region of the nozzle 17 through the base end. The magnetic tip cover 25 has the fringe region 26 at the base end.

Such disposable tip 20, magnetic tip 21 (a region excluding the magnetic substance 23), and magnetic tip cover 25 can be prepared with the use of resin, such as polyethylene, polypropylene, or polycarbonate resin.

It is preferable that the nozzle mechanism 9 comprise a release mechanism for releasing the disposable tip 20, the magnetic tip 21, and the magnetic tip cover 25 mounted on the apical end 18 or middle region 19 (not shown). Examples of release mechanisms that can be employed include pressing region that push downward the fringe region 22 of the disposable tip 20, the fringe region 24 of the magnetic tip 21, and the fringe region 26 of the magnetic tip cover 25.

The reagent rack 3 of the sample processing device is in a form of a box capable of accommodating a plurality of reagent bottles. The reagent rack 3 is capable of accommodating different reagent bottles depending on specific type of processing performed on biological samples. When nucleic acid components are extracted from biological samples, for example, the reagent rack 3 can accommodate a reagent bottle of a solution containing a chaotropic agent, a reagent bottle of a wash solution, a reagent bottle of an eluent, and a reagent bottle of oil dispensed into the reaction container 2. Also, the number of reagent bottles of the same type accommodated in the reagent rack 3 may be the same as the number of the plurality of nozzles 17 provided in the nozzle mechanism 9. In such a case, reagent bottles of the same type are arranged so as to fit into spaces between the plurality of nozzles 17.

The analyte rack 4 of the sample processing device is in the form of a box capable of accommodating the plurality of analyte tubes filled with the same or different biological samples. The plurality of analyte tubes are arranged in the analyte rack 4 disposed so as to fit into spaces between the plurality of nozzles 17.

The magnetic tip rack 5 of the sample processing device comprises a plurality of openings accommodating the plurality of magnetic tips 21 shown in FIG. 7. The diameter of such openings is somewhat larger than the outer diameter of the magnetic tip 21 and somewhat smaller than that of the fringe region 24. Such plurality of openings are arranged so as to fit into spaces between the plurality of nozzles 17. Specifically, a plurality of openings form a line in such a manner that spaces between the centers of the plurality of openings are approximately equal to spaces between the centers of the apical ends of the plurality of nozzles 17, in which the number of openings is the same as or a multiple of that of the nozzles, and multiple columns of such line are aligned.

The cover rack 6 of the sample processing device comprises a plurality of openings accommodating the plurality of magnetic tip covers 25 shown in FIG. 8. The diameter of such openings is somewhat larger than the outer diameter of the magnetic tip cover 25 and somewhat smaller than that of the fringe region 26. Such plurality of openings are arranged so as to fit into spaces between the plurality of nozzles 17. Specifically, a plurality of openings form a line in such a manner that spaces between the centers of the plurality of openings are approximately equal to spaces between the centers of the apical ends of the plurality of nozzles 17, in which the number of openings is the same as or a multiple of that of the nozzles, and multiple columns of such line are aligned.

The tip rack 7 of the sample processing device comprises a plurality of openings accommodating the plurality of disposable tips 20 shown in FIG. 6. The diameter of such openings is somewhat larger than the outer diameter of the disposable tip 20 and somewhat smaller than that of the fringe region 22. Such plurality of openings are arranged so as to fit into spaces between the plurality of nozzles 17. Specifically, a plurality of openings form a line in such a manner that spaces between the centers of the plurality of openings are approximately equal to spaces between the centers of the apical ends of the plurality of nozzles 17, in which the number of openings is the same as or a multiple of that of the nozzles, and multiple columns of such line are aligned.

The waste container 8 of the sample processing device is a box-shaped container used for discarding the used disposable tip 20, magnetic tip 21, magnetic tip cover 25, biological samples after processing, wash solution, or the like. It is preferable that the waste container 8 be provided with a release mechanism for releasing the disposable tip 20, the magnetic tip 21, and the magnetic tip cover 25 provided in the apical end 18 or middle region 19 of the nozzle 17 (not shown). An example of a release mechanism that can be employed is a pressing plate that is positioned to abut the fringe region 22 of the disposable tip 20, the fringe region 24 of the magnetic tip 21, and the fringe region 26 of the magnetic tip cover 25 and drives the nozzle 17 upward so as to press the fringe regions 22, 24, and 25 downward. It is sufficient for the release mechanism to be provided in either the nozzle mechanism 9 or the waste container 8.

The drive control unit 10 of the sample processing device comprises a drive mechanism comprising a power source such as a motor, a gear mechanism that transmits power supplied from the power source, an arm or the like, and a control board that output a control signal, which allows the nozzle mechanism 9 to move along the x-axis, the y-axis, and the z-axis and to rotate around the z-axis shown in FIG. 1, to the drive mechanism (not shown). Various conditions set by an operator through the computer (not shown) are inputted into the control board.

Figure 9:
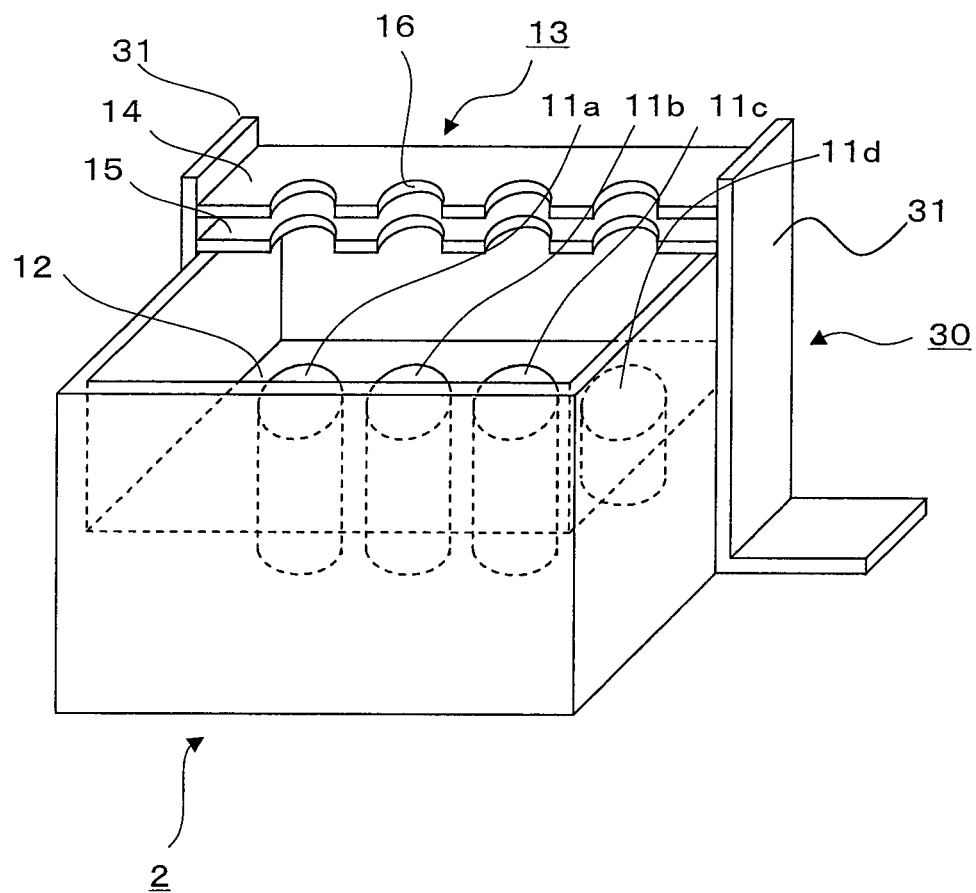
FIG. 9 is a perspective view showing a cover-removing mechanism and a reaction container of the sample processing device.

It should be noted that the present invention is not limited to the sample processing device having the constitution described above. The sample processing device described above comprises the reaction container 2 having the cover-removing mechanism 13 mounted on the stage 1. However, the sample processing device may comprise the cover-removing mechanism 13 at a position at which the reaction container 2 is to be mounted. That is, the sample processing device may comprise the cover-removing mechanism 13. Specifically, the sample processing device comprises the cover retainer 30 equipped with the cover-removing mechanism 13 at a position at which the reaction container 2 is to be mounted on one surface of the stage 1, as shown in FIG. 9. The cover retainer 30 is composed of a pair of side surfaces 31 with an L-shaped cross-section and the cover-removing mechanism 13 positioned at a given level with the aid of the pair of side surfaces 31. The cover retainer 30 may comprise a mechanism that is removable from the stage 1 (not shown). The sample processing device comprising the cover retainer 30 involves the use of a reaction container 2 having a similar constitution, except that it does not comprise the cover-removing mechanism 13. When a plurality of reaction containers 2 are mounted on the sample processing device, the sample processing device would comprise a plurality of cover retainers 30 corresponding to the reaction containers 2.

The cover retainer 30 may be constructed so as to allow the cover-removing mechanism 13 to move vertically (i.e., along the z-axis shown in FIG. 1) and to allow the position to be determined. In such a case, a plurality of vertically parallel concave grooves are provided on one surface of each of the pair of side surfaces 31 opposed to the other, and the cover-removing mechanism 13 can move vertically along the concave grooves. In such a case, it is preferable that the cover retainer 30 comprise a fixation means, such as a pin, in order to fix the cover-removing mechanism 13 onto the pair of side surfaces 31.

The sample processing device thus constructed is capable of performing various types of processing of biological samples. The sample processing device is described below with reference to an embodiment of extraction of nucleic acid components from biological samples. Specifically, the sample processing device enables nucleic acid extraction with the mixing of silica-coated magnetic beads with a sample containing nucleic acids and other impurities in the presence of a chaotropic agent, the allowing of nucleic acids to adsorb to the magnetic bead surfaces, the separation of the magnetic beads that had adsorbed nucleic acids, washing the separated magnetic beads, and the eluting of nucleic acids from the magnetic beads.

Figure 10:
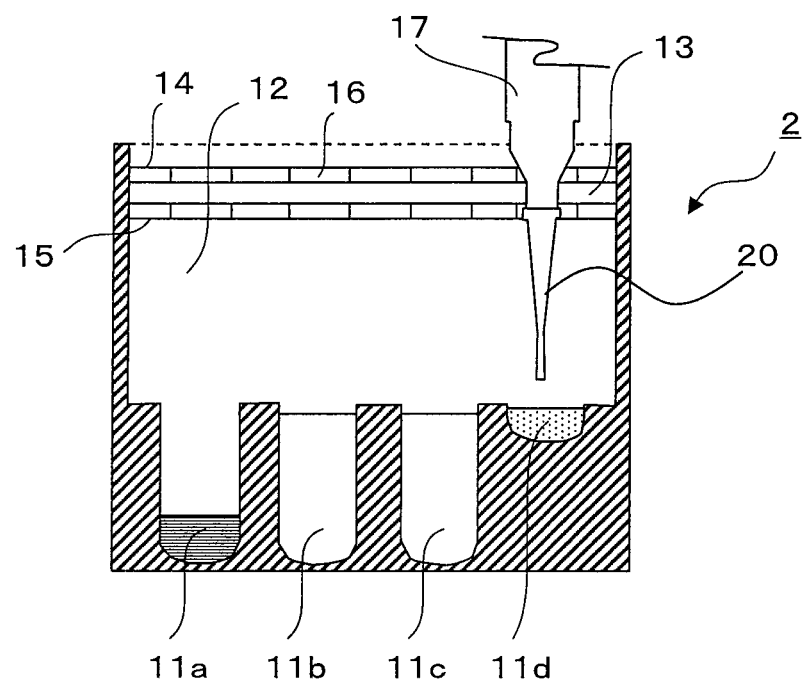
FIG. 10 is a cross-sectional view of a reaction container in the step of dispensing various liquids to a reaction container in accordance with the sample processing method of the present invention.

At the outset, more specifically, a solution containing target biological samples, a chaotropic agent, and a surfactant is dispensed into the reaction site 11$a$, a wash solution is dispensed into the reaction sites 11$b$ and 11$c$, and an eluent is dispensed into the reaction site 11$d$, as shown in FIG. 10. When dispensing such solutions into the reaction sites 11$a$ to 11$d$, the disposable tip 20 is mounted on the nozzle 17 of the nozzle mechanism 9. In order to mount the disposable tip 20 onto the nozzle 17, the drive control unit 10 first controls the nozzle mechanism 9 to migrate to a position at which the center of the base end of the disposable tip 20 accommodated in the tip rack 7 is precisely opposed to the apical end 18 of the nozzle 17 (i.e., migration in the x-axis and the y-axis directions). Subsequently, the drive control unit 10 controls the nozzle mechanism 9 to move downward (along the z-axis) so as to allow the disposable tip 20 to be mounted onto the apical end 18 of the nozzle 17. Through the above sequence of procedures, the disposable tips 20 can be mounted on the plurality of nozzles 17 of the nozzle mechanism 9.

While the disposable tip 20 remains mounted, the nozzle mechanism 9 is allowed to migrate to a position above the reagent rack 4 with the control of the drive control unit 10, the apical end of the disposable tip 20 is inserted into a reagent bottle, and a given amount of solution is suctioned via a suction/discharge drive apparatus, such as a pump means (not shown). In this case, the same number of given reagent bottles as the nozzles 17 are provided and aligned in the reagent rack. Thus, the plurality of disposable tips 20 can all simultaneously suction the solution.

Thereafter, the drive control unit 10 controls the nozzle mechanism 9 to migrate to a position above the reaction container 2, and the apical ends of the disposable tips 20 are positioned above the given reaction sites 11$a$ to 11$d$. The suction/discharge drive apparatus is activated in such state, and the solution suctioned into the disposable tips 20 can then be dispensed into given reaction sites 11$a$ to 11$d$. Upon completion of the dispensing of the solution, the drive control unit 10 controls the nozzle mechanism 9 to migrate to a position above the waste container 8, and a release mechanism mounted on the nozzle mechanism 9 or waste container 8 is activated to discard the used disposable tips 20.

The above sequence of procedures is common when dispensing a solution containing a wash solution, an eluent, a chaotropic agent, and a surfactant. Dispensing of biological samples is carried out via the above sequence of procedures, except that given amounts of biological samples are suctioned through the analyte tubes accommodated in the analyte rack 4. When a wash solution, an eluent, biological samples, a chaotropic agent, and a solution containing a surfactant are dispensed, different disposable tips 20 are used, respectively.

Figure 11:
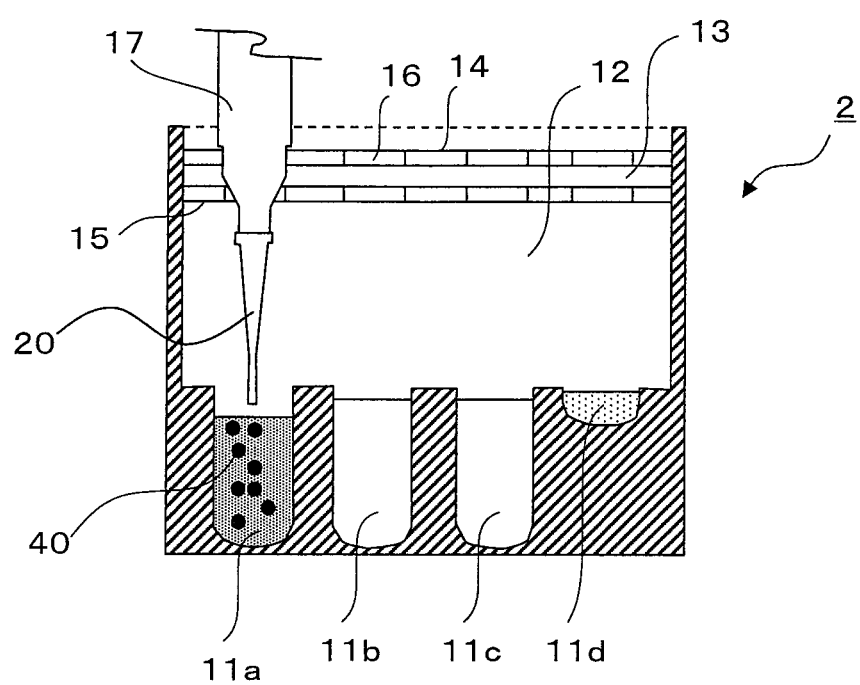
FIG. 11 is a cross-sectional view of a reaction container in the step of dispensing magnetic beads to a reaction container in accordance with the sample processing method of the present invention.

Subsequently, silica-coated magnetic beads 40 are dispensed into the reaction site 11$a$ into which the target biological samples have been dispensed, as shown in FIG. 11. The magnetic beads 40 may be dispensed into the reaction site 11$a$ in advance, or a solution comprising magnetic beads dispersed therein may be dispensed into the reaction site 11$a$ in the same manner as with the case of the nozzle mechanism 9. While biological samples are dispensed at the step shown in FIG. 10, biological samples may be dispensed simultaneously or successively with the magnetic beads 40 in this step.

Beads of any materials, configurations, and particle diameters can be used as the magnetic beads 40, provided that such beads have features of magnetic substances that have been commonly used in the biotechnology field, for example. When nucleic acid extraction is carried out with the use of the sample processing device, magnetic beads 40 having the capacity for nucleic acid adsorption are used. The capacity for nucleic acid adsorption can be imparted by coating magnetic bead surfaces with silica.

Since a chaotropic agent is present in the reaction site 11a in this step, nucleic acid components contained in the biological samples adsorb onto the surfaces of the silica-coated magnetic beads 40. In addition, the content of the reaction site 11a may be agitated in this step. The content of the reaction site 11a can be agitated via, for example, the method in which a periodic magnetic field is applied from the outside of the reaction container 2 to allow the magnetic beads 40 to migrate inside the reaction site 11a or the method in which the disposable tip 20 or magnetic tip cover 25 is mounted on the nozzle 17, and the drive control unit 10 controls the nozzle mechanism 9 to allow the disposable tip 20 or magnetic tip cover 25 mounted on the nozzle 17 to rotate or shake inside the reaction site 11a.

Figure 12:
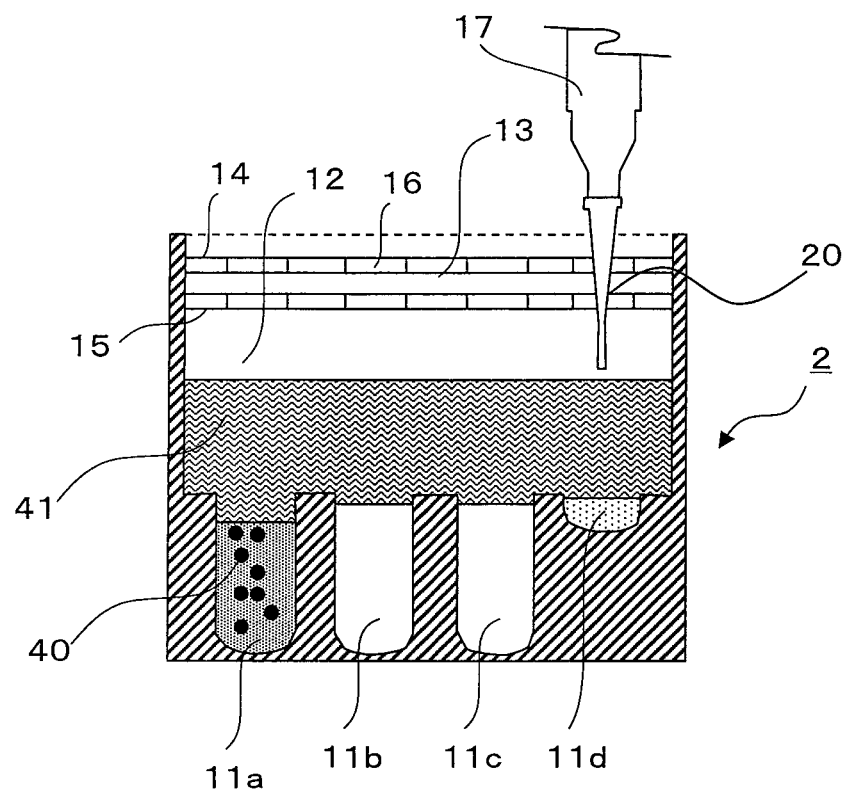
FIG. 12 is a cross-sectional view of a reaction container in the step of dispensing oil to a reaction container in accordance with the sample processing method of the present invention.

Oil 41 is then dispensed into an empty space 12 of the reaction container 2, as shown in FIG. 12. General machine oil, mineral oil, silicon oil, fluorinated oil, and the like can be used as the oil 41. Use of mineral oil is preferable from the viewpoint of nucleic acid extraction. Oil 41 can be dispensed into the empty space 12 in the same manner as with the case of dispensing of a solution implemented by the nozzle mechanism 9 with the control of the drive control unit 10. A sufficient amount of the oil 41 is dispensed into the empty space 12 located above the reaction sites 11a to 11d, so that the oil can prevent evaporation of various solutions dispensed into the reaction sites 11a to 11d or contamination caused by droplet scattering. Since the amount of the oil 41 dispensed is larger than that of various solutions described above, other higher-capacity disposable tips may be prepared and used.

Figure 13:
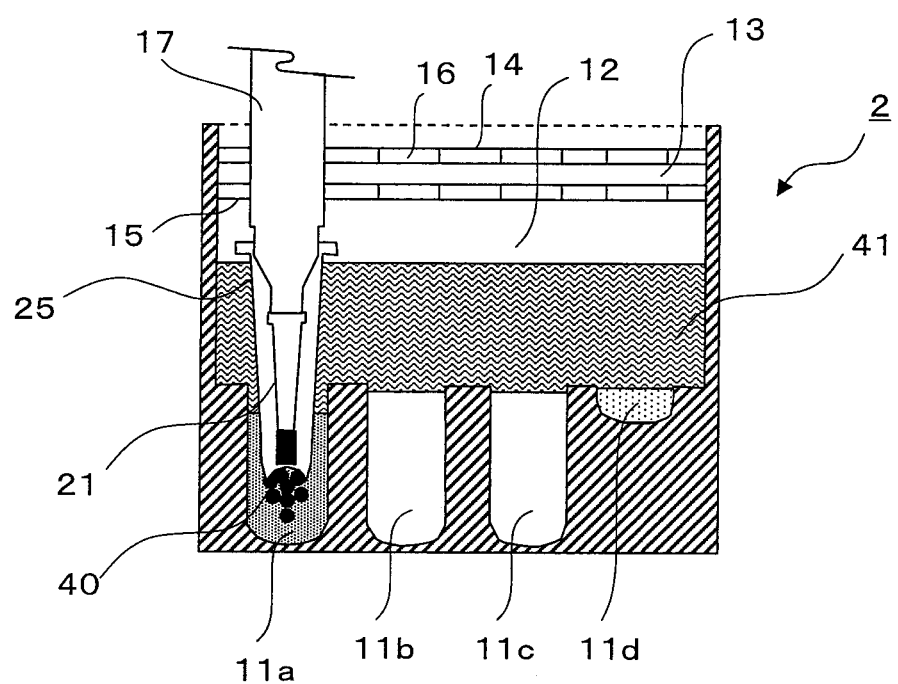
FIG. 13 is a cross-sectional view of a reaction container in the step of capturing magnetic beads in accordance with the sample processing method of the present invention.

Subsequently, the magnetic tip 21 and the magnetic tip cover 25 are mounted on the nozzle 17 to capture the magnetic beads 40 at the reaction site 11a at the apical end of the magnetic tip cover 25, as shown in FIG. 13. In this step, the magnetic tip 21 and the magnetic tip cover 25 can be mounted on the nozzle 17 in the same manner as with the case of mounting of the disposable tip 20 on the nozzle 17 by controlling the nozzle mechanism 9 with the drive control unit 10 described above. The magnetic tip cover 25 is mounted on the middle region 19 of the nozzle 17 after the magnetic tip 21 has been mounted on the apical end 18 of the nozzle 17. In this step, apical ends of the magnetic tip 21 and the magnetic tip cover 25 may be allowed to rotate, shake, or move vertically inside the reaction site 11a. Thus, magnetic beads 40 can be securely captured at the apical end of the magnetic tip cover 25. The apical ends of the magnetic tip 21 and the magnetic tip cover 25 can be made to rotate, shake, or move vertically inside the reaction site 11a by controlling the nozzle mechanism 9 with the drive control unit 10.

Figure 14:
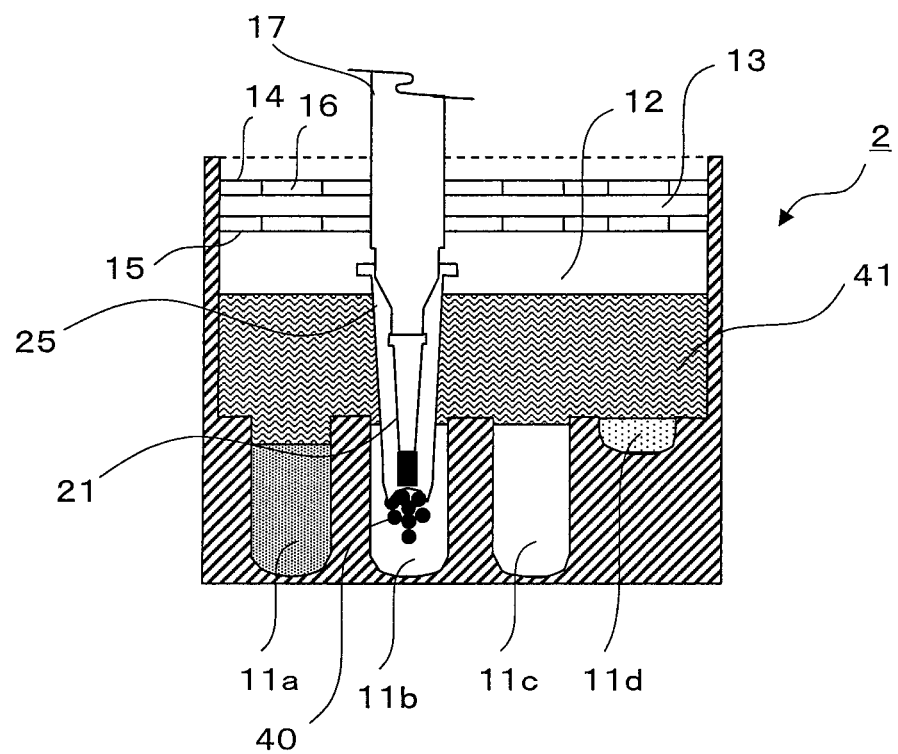
FIG. 14 is a cross-sectional view of a reaction container in the step of transporting magnetic beads in accordance with the sample processing method of the present invention.

The drive control unit 10 then controls the nozzle mechanism 9 to allow the apical ends of the magnetic tip 21 and the magnetic tip cover 25 to migrate from the reaction site 11a to the reaction site 11b while the magnetic beads 40 remain captured, as shown in FIG. 14. In this case, the magnetic tip 21 and the magnetic tip cover 25 migrate inside the empty space 12 while refraining from contact with the cover-removing mechanism 13. In this step, the magnetic tip cover 25 that had captured the magnetic beads 40 migrates inside the oil 41 dispensed into the empty space.

When the magnetic beads 40 are captured at the apical end of the magnetic tip cover 25 in the reaction site 11a, a solution containing proteins other than nucleic acids or other impurities adheres to the periphery of the magnetic tip cover 25 or a space among the aggregated magnetic beads 40. If the magnetic tip cover 25 that had captured the magnetic beads 40 migrates inside the oil 41 as described above, the solution adhering to the periphery of the magnetic tip cover 25 or the space among the aggregated magnetic beads 40 can be removed. Even if a solution containing impurities is present in the space among the aggregated magnetic beads 40, for example, such solution is replaced with the oil 41 by passing through the oil 41. This can prevent the solution dispensed into the reaction site 11a from being carried over the reaction site 11b.

When picking up the magnetic tip cover 25 and the magnetic beads 40 that had been captured at the end thereof from the reaction site 11a, generation of droplets or mist can be prevented since the oil 41 has been dispensed into the empty space 12. Even if the oil 41 is absent in the empty space 12, droplets or mist of the solution dispensed into the reaction site 11a would be generated by the picking up the magnetic tip cover 25 and the magnetic beads 40 that had been captured at the end thereof from the reaction site 11a. The droplets or mist generated would reach the adjacent reaction container 2, as well as the adjacent reaction site 11b, resulting in contamination. That is, dispensing of the oil 41 into the empty space 12 can prevent contamination with certainty, and it enables the performance of more precise forms of nucleic acid extraction.

Figure 15:
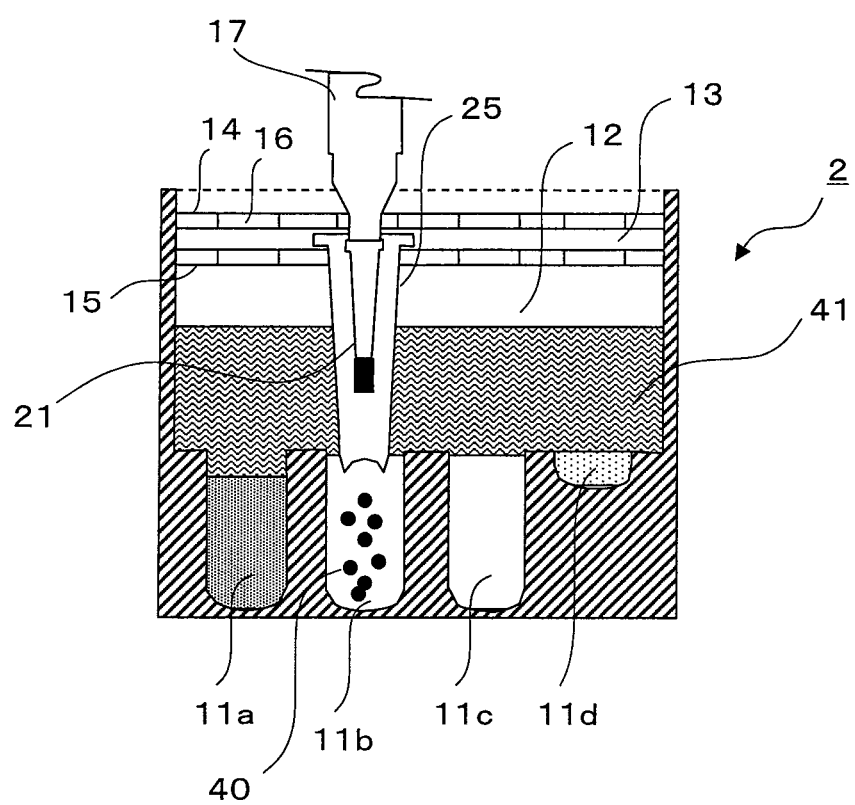
FIG. 15 is a cross-sectional view of a reaction container in the step of removing the magnetic beads captured by the sample processing method of the present invention.
Figure 16:
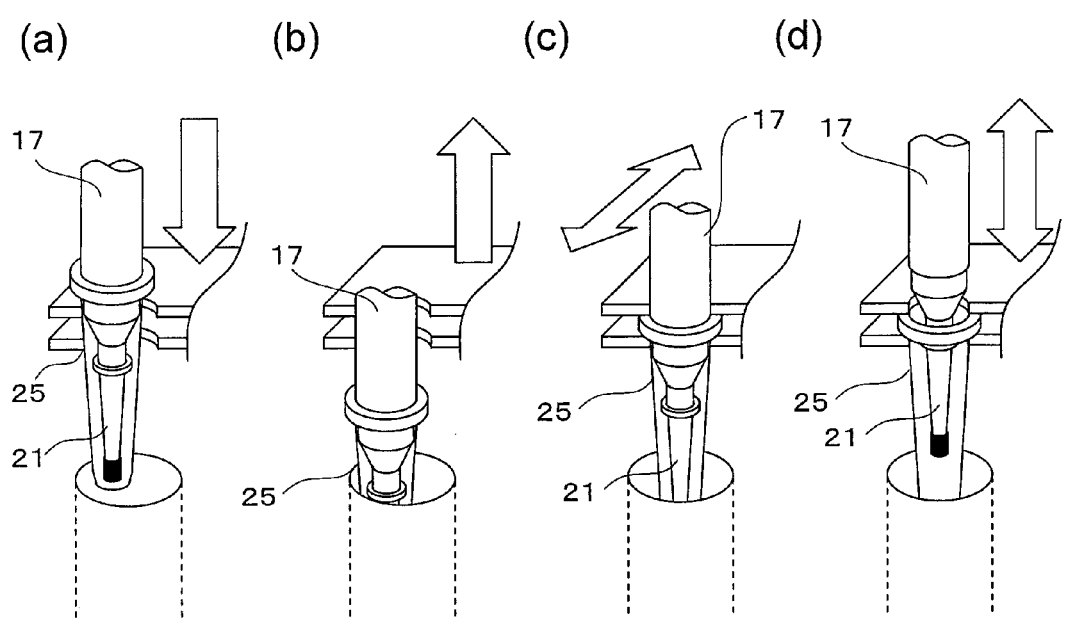
FIG. 16 is a perspective view showing the principles of a nozzle and a cover-removing mechanism in the step of removing the magnetic beads captured by the sample processing method of the present invention.

Subsequently, the drive control unit 10 controls the nozzle mechanism 9 to remove the magnetic beads 40 from the apical end of the magnetic tip cover 25 with the utilization of the cover-removing mechanism 13, as shown in FIG. 15. FIG. 16 (A) to (D) shows the procedure of inserting the magnetic tip cover 25 into the reaction site 11b while capturing the magnetic beads 40 and removing the magnetic beads 40 from the apical end of the magnetic tip cover 25.

At the outset, the drive control unit 10 controls the nozzle mechanism 9 to insert the apical end of the nozzle 17 on which the magnetic tip 21 and the magnetic tip cover 25 have been mounted into the reaction site 11b (downward along the z-axis), as shown in FIG. 16 (A). Subsequently, the apical end of the nozzle 17 on which the magnetic tip 21 and the magnetic tip cover 25 have been mounted is lifted from the inside of the reaction site 11b (upward along the z-axis), as shown in FIG. 16 (B).

As shown in FIG. 16 (C), the nozzle 17 is lifted until the fringe region 26 of the magnetic tip cover 25 reaches the position between the upper retainer plate 14 and the lower retainer plate 15 of the cover-removing mechanism 13, and it is then allowed to migrate, so that the magnetic tip cover 25 fits into the notch region 16 (in the y-axis direction). This migration leads the fringe region 26 of the magnetic tip cover 25 to be inserted and latched in a position between the upper retainer plate 14 and the lower retainer plate 15. When the reaction container 2 is observed from above, the notch region 16 is provided in such a manner that the end surface thereof is positioned to the inside of the openings of the reaction sites 11a to 11d. Thus, the magnetic tip cover 25 can be securely fitted into the notch region 16 without contact between the periphery of the magnetic tip cover 25 and the side surface of the reaction site 11b.

Subsequently, as shown in FIG. 16 (D), the drive control unit 10 controls the nozzle mechanism 9 to further lift the nozzle 17 (upward along the z-axis). By such lifting, the upper surface of the fringe region 26 of the magnetic tip cover 25 mounted on the nozzle 17 is latched together by the upper retainer plate 14, and only the magnetic tip cover 25 is separated from the nozzle 17. Since the magnetic tip 21 mounted on the nozzle 17 is lifted upward together with the nozzle 17, magnetic beads captured at the apical end of the magnetic tip cover 25 are removed from the apical end, and the magnetic beads are then deposited at the bottom of the reaction site 11b (FIG. 15). With the use of the cover-removing mechanism 13, the magnetic tip cover 25 can be removed from the nozzle 17 and retained while the apical ends of the magnetic tip cover 25 remain inserted into the reaction sites 11a to 11d.

As described above, it is sufficient for the drive control unit 10 to control the nozzle mechanism 9 to allow the magnetic beads 40 inside the reaction site 11a to migrate to the reaction site 11b. This eliminates the necessity of removal of a solution from the reaction site 11a and facilitates migration of the magnetic beads 40.

The magnetic beads 40 can be washed with a wash solution dispensed into the reaction site 11b, and impurities, such as proteins derived from biological samples, can be removed from the surfaces of the magnetic beads 40 under the conditions shown in FIG. 15. In this step, the wash solution in the reaction site 11b may be agitated in order to further enhance the washing efficiency. The contents of the reaction site 11b can be agitated by, for example, a method in which a periodic magnetic field is applied from the outside of the reaction container 2 to allow the magnetic beads 40 to migrate inside the reaction site 11b or a method in which the magnetic tip 21 mounted on the nozzle 17 is removed, and the magnetic tip cover 25 retained by the cover-removing mechanism 13 is mounted on the nozzle 17 again to allow the magnetic tip cover 25 to rotate or shake inside the reaction site 11b. The magnetic tip cover 25 can be mounted on the nozzle 17 by reversely performing the sequence of procedures shown in FIG. 16 (A) to (D).

Figure 17:
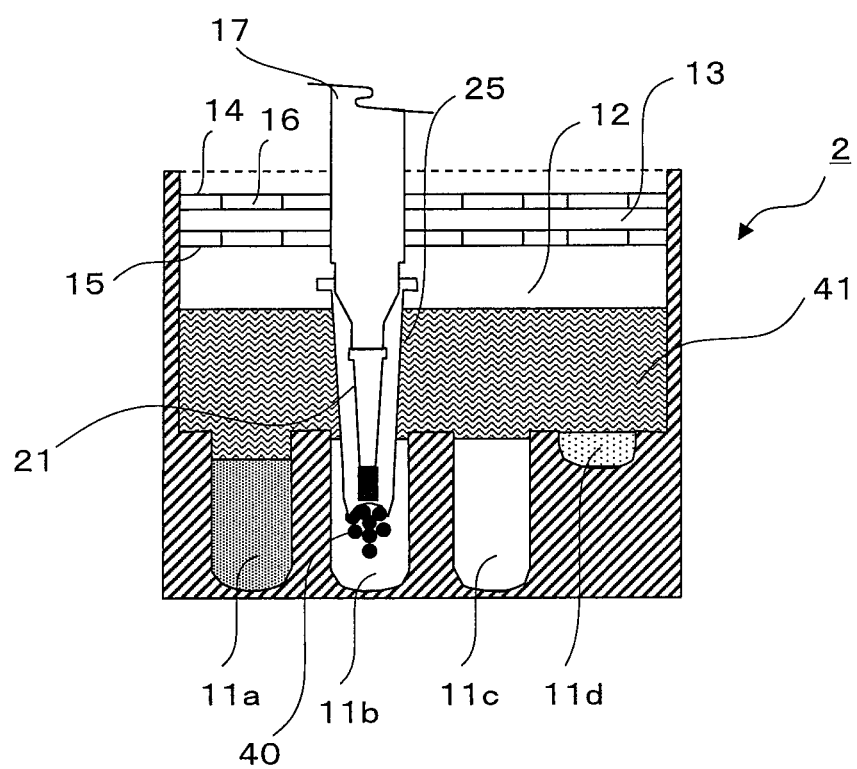
FIG. 17 is a cross-sectional view showing a reaction container in the step of capturing magnetic beads in accordance with the sample processing method of the present invention.

Subsequently, the magnetic beads 40 washed in the reaction site 11b are captured at the apical end of the magnetic tip cover 25 again, as shown in FIG. 17. This step can be carried out by controlling the nozzle mechanism 9 with the drive control unit 10, as with the case of the step shown in FIG. 13.

Figure 18:
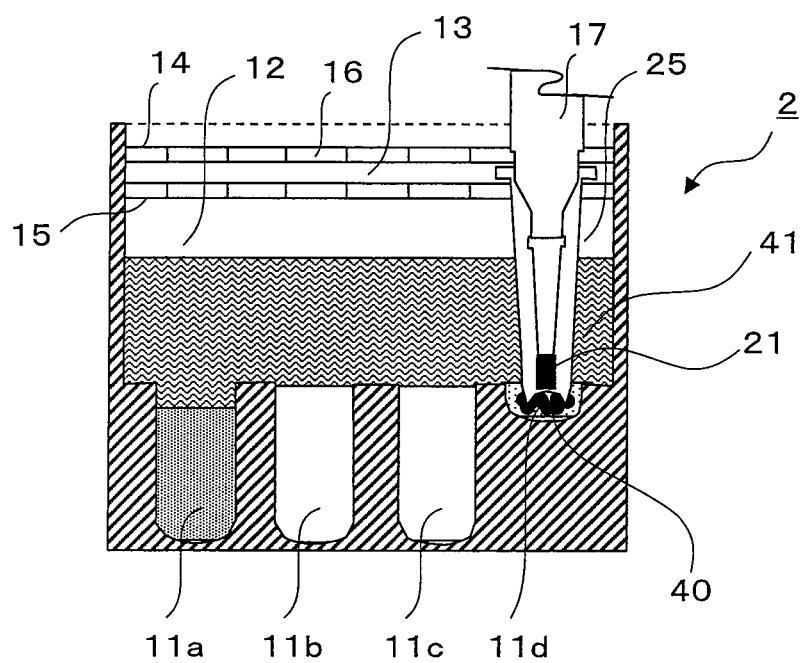
FIG. 18 is a cross-sectional view showing a reaction container in the step of transporting magnetic beads into an eluent in accordance with the sample processing method of the present invention.

Subsequently, the magnetic beads 40 captured at the apical end of the magnetic tip cover 25 are subjected to a second washing at the reaction site 11c (not shown), and the magnetic beads 40 captured at the apical end of the magnetic tip cover 25 are allowed to migrate to the reaction site 11d into which an eluent has been dispensed, as shown in FIG. 18. This step can be carried out by controlling the nozzle mechanism 9 with the drive control unit 10, as with the case of the step shown in FIG. 14.

Figure 19:
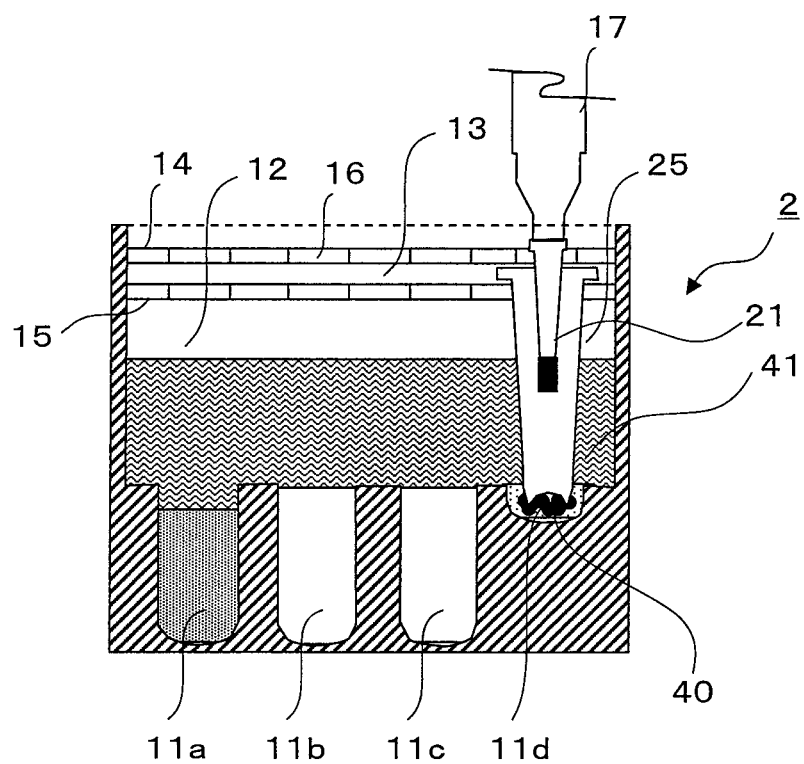
FIG. 19 is a cross-sectional view showing a reaction container in the step of soaking magnetic beads in an eluent in accordance with the sample processing method of the present invention.
Figure 20:
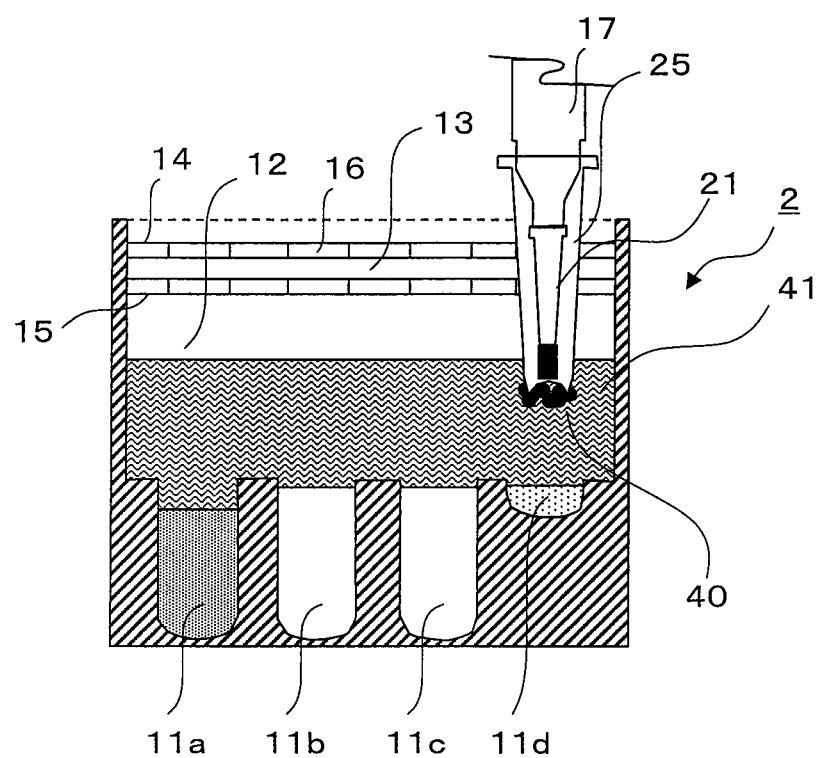
FIG. 20 is a cross-sectional view showing a reaction container in the step of recovering magnetic beads from an eluent in accordance with the sample processing method of the present invention.

Subsequently, the drive control unit 10 controls the nozzle mechanism 9 to remove the magnetic beads 40 from the apical end of the magnetic tip cover 25 with the cover-removing mechanism 13, as shown in FIG. 19. These steps can be carried out by controlling the nozzle mechanism 9 with the drive control unit 10, as with the case of the steps shown in FIG. 15 and FIG. 16. In this step, nucleic acid components adsorbed to the surfaces of the magnetic beads 40 can be eluted in the eluent. In the end, the magnetic beads 40 in the eluent are captured at the apical end of the magnetic tip cover 25 again as shown in FIG. 20, as with the case of the step shown in FIG. 17. The drive control unit 10 controls the nozzle mechanism 9 to migrate to a space above the waste container 8, and the release mechanism mounted on the nozzle mechanism 9 or the waste container 8 is activated to discard the magnetic tip cover 25 and the magnetic tip 21 while the magnetic beads 40 remain captured at the apical end.

Figure 21:
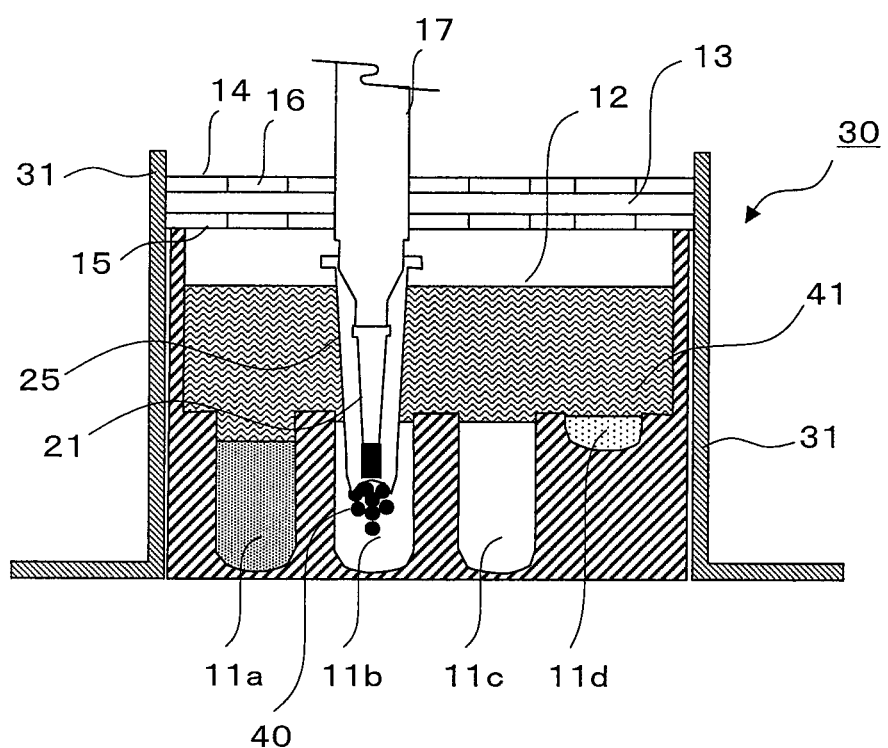
FIG. 21 is a cross-sectional view showing a cover-removing mechanism and a reaction container in the step of transporting magnetic beads with the use of the sample processing device and the reaction container shown in FIG. 9.
Figure 22:
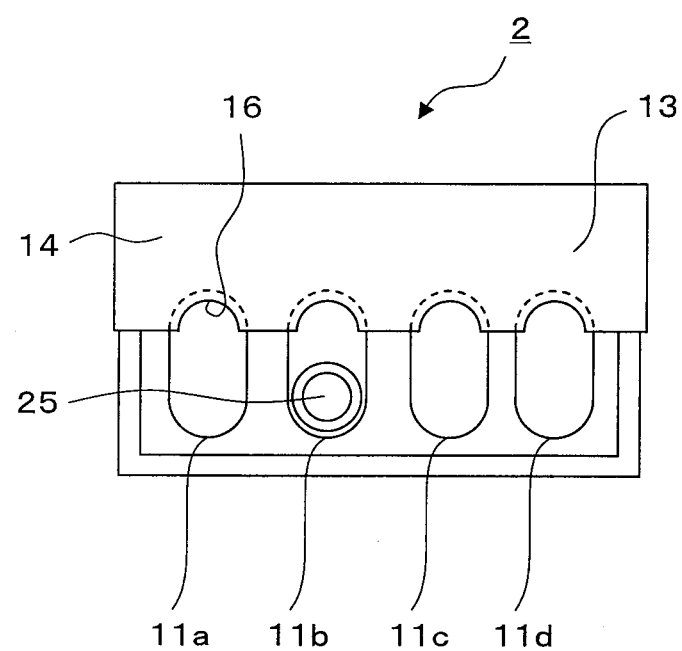
FIG. 22 is a top view showing a cover-removing mechanism and a reaction container in the step of transporting magnetic beads with the use of the sample processing device and the reaction container shown in FIG. 9.

With the use of the sample processing device shown in FIG. 9, nucleic acid extraction can also be carried out in the manner described with reference to FIG. 10 to FIG. 20. As shown in FIGS. 21 and 22, specifically, the magnetic beads 40 captured at the apical end of the magnetic tip cover 25 are allowed to migrate to the reaction site 11b, and the magnetic beads 40 can then be allowed to migrate from the reaction site 11b to the reaction site 11c. As shown in FIG. 22, the opening ends of the reaction sites 11a to 11d may be oval. The oval opening ends of the reaction sites 11a to 11d can prevent interference with the cover retainer 30 certainly by the movement of the nozzle 17 equipped with the disposable tip 20 and the magnetic tip cover 25.

Figure 23:
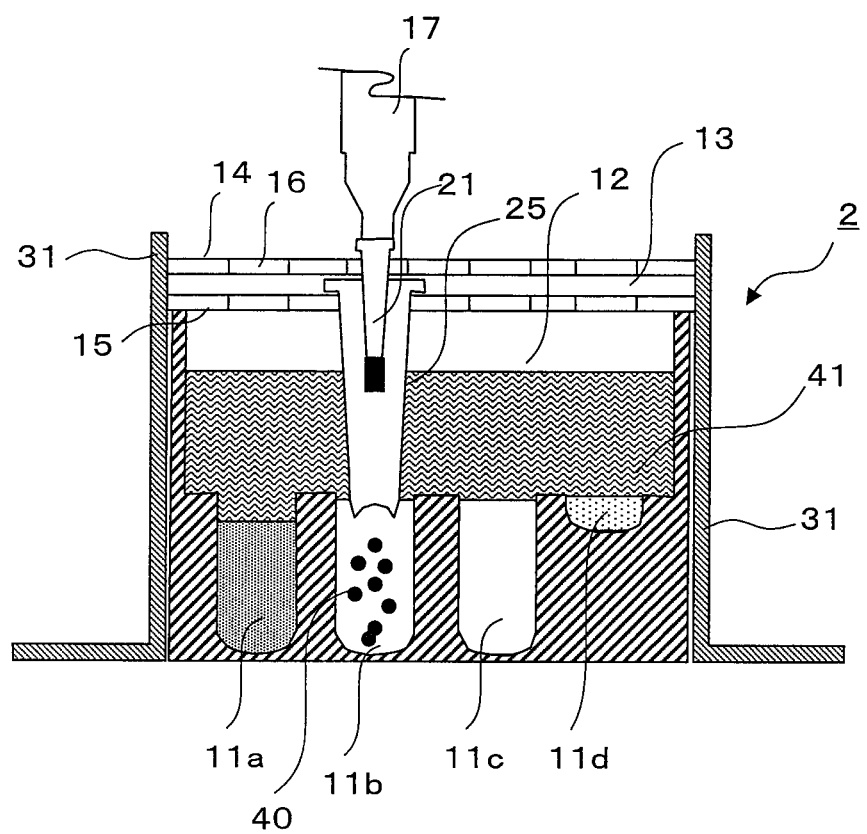
FIG. 23 is a cross-sectional view showing a cover-removing mechanism and a reaction container in the step of removing the captured magnetic beads with the use of the sample processing device and the reaction container shown in FIG. 9.
Figure 24:
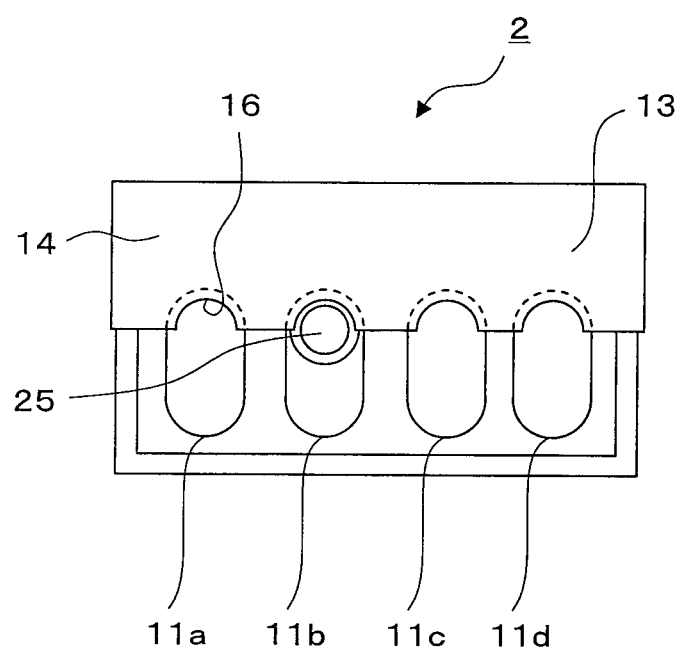
FIG. 24 is a top view showing a cover-removing mechanism and a reaction container in the step of removing the captured magnetic beads with the use of the sample processing device and the reaction container shown in FIG. 9.

When the sample processing device shown in FIG. 9 is used, the magnetic beads captured at the apical end of the magnetic tip cover 25 can be also removed with the use of the cover-removing mechanism 13 of the cover retainer 30, as shown in FIGS. 23 and 24.

As described above, the magnetic beads 40 are allowed to transit from a given step of processing to the subsequent step of processing, but the magnetic beads 40 that had adsorbed nucleic acids pass through the oil 41 in the sequence of processing according to the method of nucleic acid extraction involving the use of the sample processing device. Thus, a highly purified nucleic acid solution can be obtained without contamination with drugs such as the chaotropic agent, the surfactant, or ethanol or isopropanol contained in the wash solution used for nucleic acid extraction. Such drugs are known to inhibit PCR and various subsequent enzyme reactions. Since the method described above is capable of removal of such drugs with higher certainty than conventional techniques, the resulting nucleic acid solution can be used for PCR, other enzyme reactions, or the like without any processing.

According to the method of nucleic acid extraction involving the use of the sample processing device, the magnetic beads 40 are captured at the apical end of the magnetic tip cover 25 and allowed to migrate to reaction sites 11a to 11d. According to conventional techniques for allowing magnetic beads to migrate via suction and discharge of the magnetic beads 40 contained in the solution with the use of tips, occasionally, magnetic beads cannot be completely suctioned into tubes located on the middle of the liquid suction line. In addition, magnetic beads are discharged together with unnecessary solution when discharging such solution from the tubes. As a result, magnetic beads would be lost disadvantageously. According to the method of nucleic acid extraction involving the use of the sample processing device described above, however, the magnetic beads 40 would not be lost, and nucleic acid extraction can be carried out in a cost-effective manner.

In addition, the drive control unit 10 and the nozzle mechanism 9 of the sample processing device have functions of dispensing biological samples and various solutions (e.g., a wash solution) and functions of allowing magnetic beads to migrate to the reaction sites 11a to 11d. In other words, the mechanism for dispensing biological samples and various solutions (e.g., a wash solution) and the mechanism for allowing magnetic beads to migrate to the reaction sites 11a to 11d are driven by the same systems (i.e., the drive control unit 10 and the nozzle mechanism 9). Thus, the constitution of the sample processing device can be simplified, and inconveniences such as inhibition of operations caused by the presence of a plurality of drive systems can be avoided.

Figure 25:
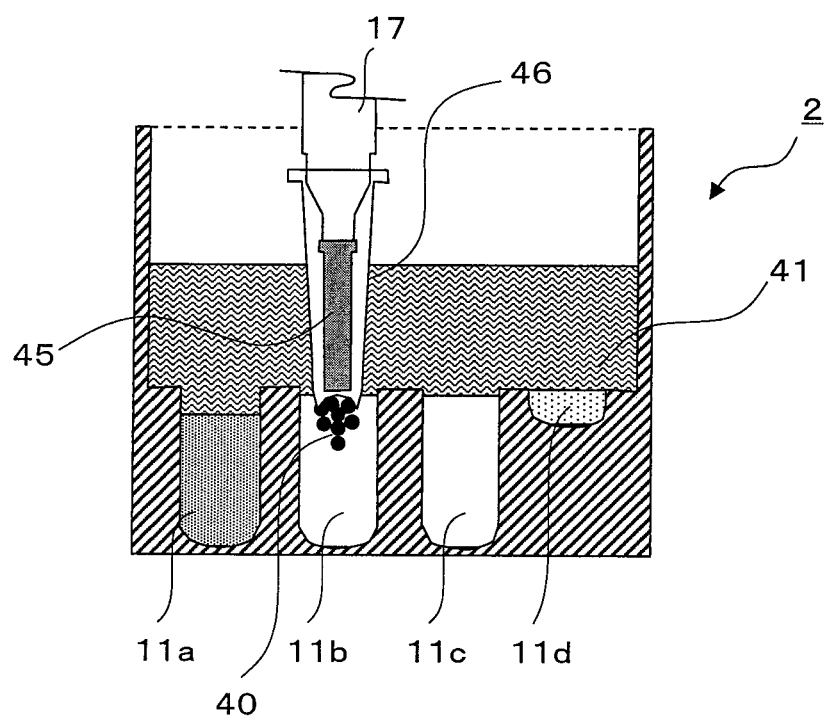
FIG. 25 is a cross-sectional view showing a reaction container in the step of capturing magnetic beads with the use of an electromagnetic tip.
Figure 26:
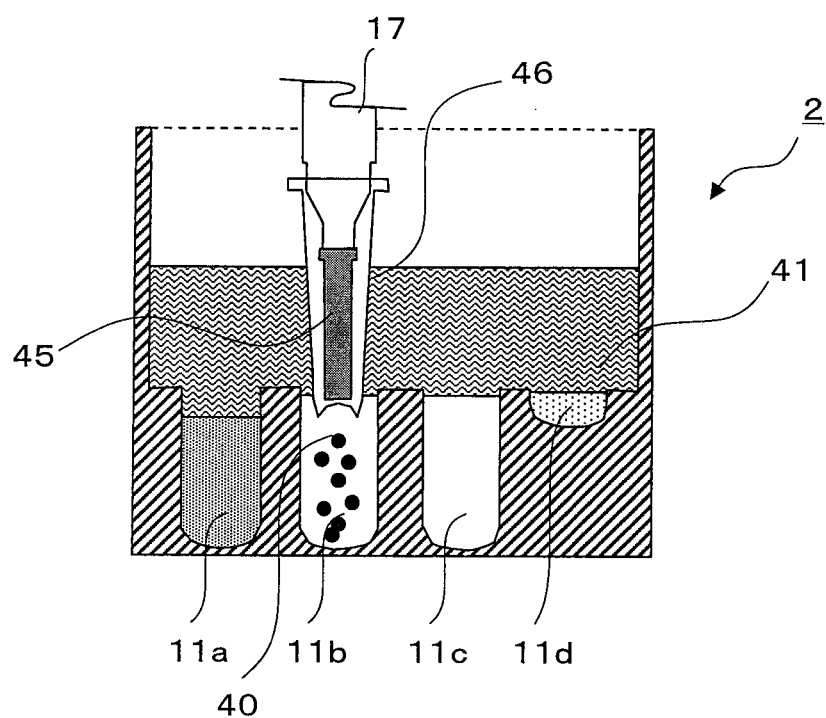
FIG. 26 is a cross-sectional view showing a reaction container in the step of removing the magnetic beads captured with the use of the electromagnetic tip.

It should be noted that the excellent effects attained by the fact that the passage of the magnetic beads through the oil 41 and the effects attained by the fact that the mechanism for dispensing various solutions and the mechanism for allowing magnetic beads to migrate are driven by the same systems are not limited to the sample processing device comprising the reaction container 2 equipped with the cover-removing mechanism 13 or the sample processing device comprising the cover-removing mechanism 13. As shown in FIGS. 25 and 26, specifically, a sample processing device that captures the magnetic beads 40 at the apical end of the electromagnetic tip cover 46 with the use of the electromagnetic tip 45 instead of the magnetic tip 21 eliminates the need for the cover-removing mechanism 13. The sample processing device shown in FIGS. 25 and 26 comprises a control unit that controls the switching of power supplied to the electromagnetic tip 45 (not shown). The sample processing device shown in FIGS. 25 and 26 can capture magnetic beads 40 at the apical end of the electromagnetic tip cover 46 by turning on the power supply to the electromagnetic tip 45. In addition, the magnetic beads 40 captured at the apical end of the electromagnetic tip cover 46 can be removed by turning off the power supplied to the electromagnetic tip 45 in the case of the sample processing device shown in FIGS. 25 and 26.

In the sample processing device having such constitution, the magnetic beads 40 pass through the oil 41 to migrate to reaction sites 11a to 11d, as described above. Accordingly, the sample processing device having such constitution can be used to prepare a highly-purified nucleic acid solution that can be used for PCR or other enzyme reactions. In addition, the sample processing device having such constitution is capable of preventing of the magnetic beads 40 from being lost and allows performance of nucleic acid extraction in a cost-effective manner. Further, the sample processing device having such constitution allows the realization of a simplified constitution of a device and the inhibition of operations caused by the presence of a plurality of drive systems.

DESCRIPTION OF THE NUMERAL REFERENCES

1: Stage; 2: reaction container; 3: reagent rack; 4: analyte rack; 5: magnetic tip rack; 6: cover rack; 7: tip rack; 8: waste container; 9: nozzle mechanism; 10: drive control unit; 11a to 11d: reaction sites; 12: empty space; 13: cover-removing mechanism; 14: upper retainer plate; 15: lower retainer plate; 16: notch region; 17: nozzle; 18: apical end; 19: middle region; 20: disposable tip; 21: magnetic tip; 22: fringe region; 23: magnetic substance; 24: fringe region; 25: magnetic tip cover; 26: fringe region; 30: cover retainer; 31: side surface; 40: magnetic beads; 41: oil; 45: electromagnetic tip; 46: the electromagnetic tip cover All publications, patents, and patent applications cited herein are incorporated herein by reference in their entirety.

The invention claimed is:

1. A sample processing device capable of placing a reaction container having a plurality of reaction sites, which comprises:
   a nozzle mechanism with a nozzle capable of attaching and removing a dispenser tip for dispensing a solution into the reaction sites of the reaction container and a magnetic tip for generating a magnetic field that allows magnetic beads to migrate to a space among the plurality of reaction sites in the reaction container, the nozzle including an apical end onto which the dispenser tip and the magnetic tip are mounted and a middle region having a diameter larger than that of the apical end, wherein the middle region is capable of attaching a magnetic tip cover, the nozzle mechanism being capable of capturing, transporting, and agitating the magnetic beads; and
   a drive assembly connected to the nozzle mechanism; and
   a cover-removing mechanism provided on the reaction container, the cover-removing mechanism including an upper retainer plate and a lower retainer plate opposed to each other with an interval therebetween, so as to sandwich a fringe region of the magnetic tip cover between a lower surface of the upper retainer plate and an upper surface of the lower retainer plate, a plurality of first notch regions provided in one side surface of the upper retainer plate, and a plurality of second notch regions provided in one side surface of the lower retainer plate in positions corresponding to the first notch regions, the cover-removing mechanism removing the magnetic tip cover from the nozzle and retaining the magnetic tip cover while the apical end of the magnetic tip cover has been inserted into one of the reaction sites.

2. The sample processing device according to claim 1, which comprises a tip rack that accommodates the dispenser tip, a magnetic tip rack that accommodates the magnetic tip, and a cover rack that accommodates the magnetic tip cover.

3. The sample processing device according to claim 2, wherein the drive assembly controls the nozzle mechanism to migrate to the reaction container, the tip rack, the magnetic tip rack, and the cover rack, and controls the nozzle mechanism to migrate so as to mount the dispenser tip, the magnetic tip, and the magnetic tip cover on the nozzle.

4. The sample processing device according to claim 1, which further comprises a reagent rack that can accommodate a reagent bottle filled with a reagent used for recovering biological molecules from biological samples.

5. The sample processing device according to claim 4, wherein the biological molecules are nucleic acids, and the device recover the nucleic acids.

6. The sample processing device according to claim 1, wherein, in case that a plurality of reaction containers are placed, the nozzle mechanism comprises a plurality of nozzles corresponding to the given reaction sites in each of the plurality of the reaction containers.

* * * * *